(12) United States Patent
Delwiche et al.

(10) Patent No.: US 9,320,821 B2
(45) Date of Patent: Apr. 26, 2016

(54) METHOD FOR COUNTERACTING AMMONIA MALODOR

(75) Inventors: Jeannine Delwiche, Newtown, PA (US); Nicholas O'Leary, Pennington, NJ (US); Anthony Reichert, Somerset, NJ (US)

(73) Assignee: Firmenich SA, Geneva (CH)

( * ) Notice: Subject to any disclaimer, the term of this patent is extended or adjusted under 35 U.S.C. 154(b) by 136 days.

(21) Appl. No.: 13/997,732

(22) PCT Filed: Dec. 20, 2011

(86) PCT No.: PCT/EP2011/073360
§ 371 (c)(1),
(2), (4) Date: Jun. 25, 2013

(87) PCT Pub. No.: WO2012/084916
PCT Pub. Date: Jun. 28, 2012

(65) Prior Publication Data
US 2013/0287721 A1  Oct. 31, 2013

Related U.S. Application Data

(60) Provisional application No. 61/426,701, filed on Dec. 23, 2010.

(51) Int. Cl.
*A61L 9/01* (2006.01)
(52) U.S. Cl.
CPC .......................................... *A61L 9/01* (2013.01)
(58) Field of Classification Search
None
See application file for complete search history.

(56) References Cited

U.S. PATENT DOCUMENTS

2005/0096220 A1* 5/2005 Tepper et al. ............. 502/527.24
2008/0293806 A1* 11/2008 Perring et al. ................ 514/452

FOREIGN PATENT DOCUMENTS

| EP | 1133982 A2 | 9/2001 |
| EP | 1133982 A2 * | 9/2001 |
| WO | WO03/043728 A1 | 5/2003 |
| WO | WO2005/110499 A1 | 11/2005 |
| WO | WO2008/023142 A1 | 2/2008 |

OTHER PUBLICATIONS

Charles J. Wysocki and Paul Wise. Methods, Approaches, and Caveats for Functionally Evaluating Olefaction and Chemestheses. Chapter 1 of: "Handbook of Flavor Characterization", New York: Marcel Dekker, 2004, Edited by Katherine D. Deibler and Jeannine Delwiche, pp. 8-14.*
Smeets, M.A.M. et al. O Chem. Senses 32 (2007) pp. 11-20.
Monsé C. et al. Chem Senses 35 (2010) pp. 523-530.
Written Opinion of the International Searching Authority for PCT/EP2011/073369 (pp. 1-6).

* cited by examiner

*Primary Examiner* — Frederick Krass
*Assistant Examiner* — Michael P Cohen
(74) *Attorney, Agent, or Firm* — Winston & Strawn LLP

(57) ABSTRACT

The present invention relates to a method for counteracting ammonia malodor comprising indentifying PRMs capable of elevating the lateralization threshold of ammonia and using such ingredients in a perfume applied to surfaces or spaces exposed to ammonia or to consumer product bases comprising ammonia.

11 Claims, 1 Drawing Sheet

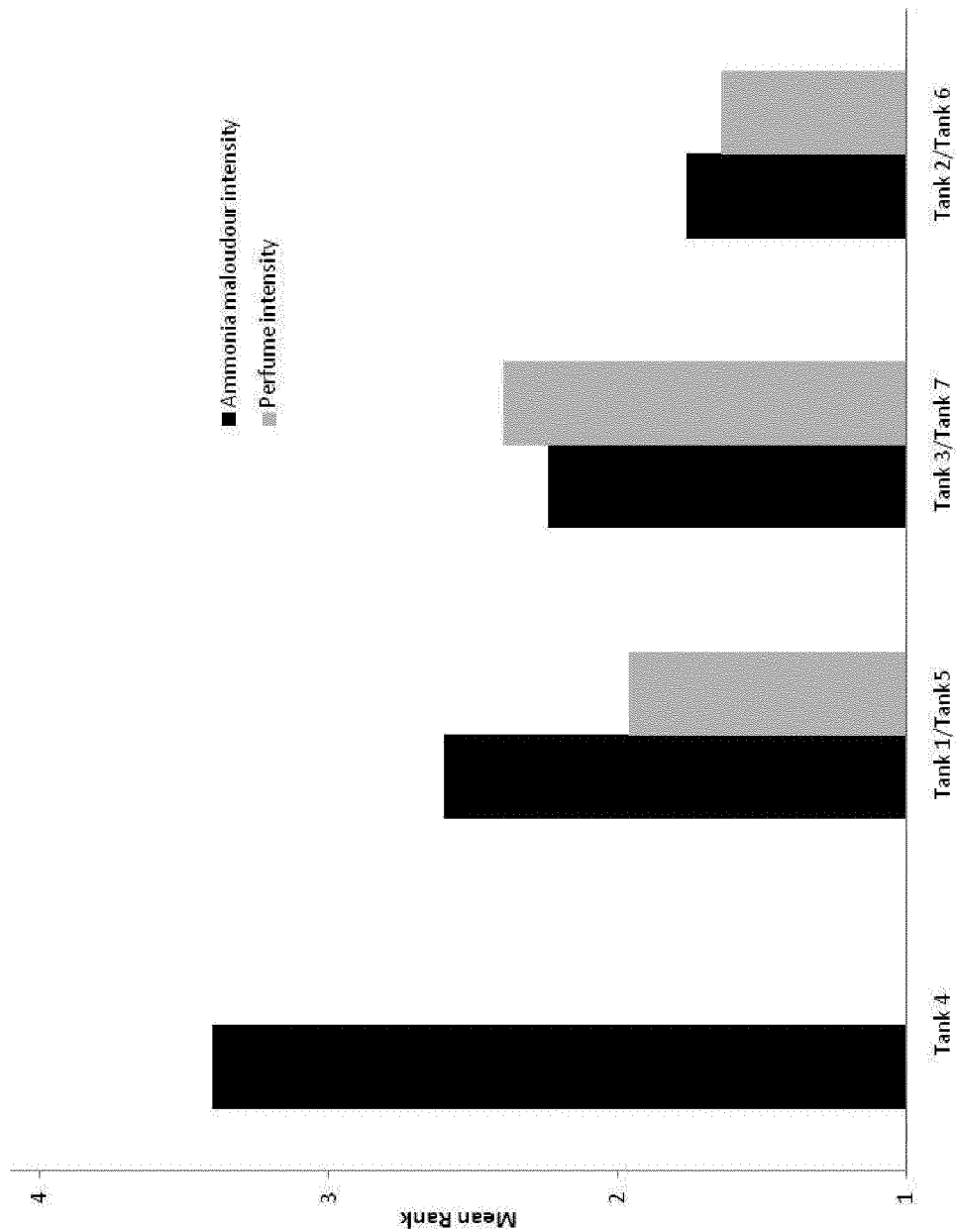

METHOD FOR COUNTERACTING AMMONIA MALODOR

TECHNICAL FIELD

The present invention relates to a method for counteracting ammonia malodor comprising indentifying PRMs capable of elevating the lateralization threshold of ammonia and using such ingredients in a perfume applied to surfaces or spaces exposed to ammonia or to consumer product bases comprising ammonia.

PRIOR ART

Constant research efforts are dedicated to the counteraction of malodors. For example, known methods counteract malodors by reacting the compounds responsible of the malodor with other chemicals so as to convert them into non-odorant or less malodorant substances and thus to reduce their perception. Other methods use substances capable of covering the malodor from an olfactive point of view.

However, no method to counteract malodor, and in particular the malodor of ammonia, is known wherein the malodor is reduced by affecting the lateralization threshold of such malodor.

Several prior art documents disclose methods for assessing the lateralization threshold of malodors such as ammonia. For example, Smeets, M. A. M., Bulsing P. J., Van Rooden, S., Steinmann, R., De Ru J. A., Ogink N. W. M., Van Thriel, C., Dalton, P. H.; O Chem. Senses 32 (2007) pp. 11-20, relates to the determination of the lateralization threshold of ammonia. However this document is completely silent with regard to ammonia malodor counteraction. The same comments apply to Monsé C., Broding, H. C., Hoffmeyer, F., Jettkant, B., Berresheim, H., Brüning, T., Bünger, J., Sucker K., Chem. Senses 35 (2010), pp. 523-530.

DESCRIPTION OF THE INVENTION

The present invention provides a method for reducing the ammonia malodor by reducing its chemesthetic potency. Chemesthesis arises when chemical compounds activate receptors just below the epithelia that mediate pain, touch and thermal perception. An odoriferous compound having chemesthetic properties, such as for example ammonia, can be perceived either by one or both nostrils. This phenomenon is called lateralization. The lateralization threshold is defined as the lowest odorant concentration that activates chemesthesis by a perceptually noticeable amount. The chemesthetic potency of odorants can be quantified by these lateralization thresholds (herein after designated as LT). The lower the LT, the more chemesthetically potent the odorant is.

The present invention therefore provides a method for counteracting ammonia malodor comprising:

a) carrying out a panel evaluation of the lateralization threshold of ammonia in the presence and in the absence of a perfumery raw material (hereinafter referred to as PRM) and comparing both lateralization thresholds;
b) identifying PRMs which elevate the ammonia lateralization threshold (Elevating PRMs);
c) creating a perfume comprising at least 30% by weight, relative to the total weight of the perfume, of one or more Elevating PRMs as identified in step b);
d) applying the perfume created in step c) to a consumer product base comprising ammonia, to a surface on which ammonia is deposited or is likely to be deposited, to the air surrounding such surfaces or to surfaces or products susceptible of generating ammonia malodor in situ as a result of urine depositing.

In step a), panellists are asked to evaluate the LT of ammonia alone. They are then asked to evaluate the LT of ammonia, when combined with a PRM. This can be done using any suitable method.

Preferably, in the first stage of the evaluation, the panellists are presented with pairs of glass bottles equipped with nose-pieces, one of these bottles containing ammonia. Each bottle is applied to one nostril, using the nosepiece. In each pair, ammonia is present in different concentrations. The panellists are asked to identify in each pair which bottle contains ammonia. The lowest concentration at which the bottle containing ammonia can be identified correctly is the ammonia lateralization threshold. In the second stage of the evaluation, the lateralization threshold of ammonia is evaluated when it is combined with a PRM using the same method. One suitable method for assessing the LT of ammonia and of ammonia combined with a PRM is exposed in further details in the examples below.

As "PRM", it is intended here any compound which is of current use in the perfumery industry, i.e. a compound which is used as active ingredient in perfuming compositions or in perfumed products in order to impart a hedonic effect into its surrounding. In other words, such compound, to be considered as being a PRM, must be recognized by a person skilled in the art of perfumery as being able to impart or modify in a positive or pleasant way the odor of a composition or product, and not just as having an odor. Moreover, this definition is also meant to include compounds that do not necessarily have an odor but are capable of modulating the odor of a perfuming composition or of a perfumed product and, as a result, of modifying the perception by a user of the odor of such a composition or product.

The nature and type of these PRMs do not warrant a more detailed description here, which in any case would not be exhaustive, the skilled person being able to select them on the basis of his general knowledge, the intended use or application and the desired organoleptic effect. In general terms, these PRMs belong to chemical classes as varied as alcohols, aldehydes, ketones, esters, ethers, acetates, nitriles, terpene hydrocarbons, nitrogenous or sulphurous heterocyclic compounds and essential oils. Said PRMs can be of natural or synthetic origin. Many of these PRMs are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said PRMs may also be compounds known to release in a controlled manner various types of perfuming compounds.

In a preferred aspect of the invention, the panel evaluation is carried out with at least 3 panellists.

Once the LT of ammonia is determined both alone and in combination with a PRM, both LTs can be compared. Based on this comparison, PRMs capable of elevating the LT of ammonia can be identified, as required in step b) of the present method. When the LT of ammonia is higher when combined with the PRM than for ammonia alone, then the PRM is identified as being capable of elevating the ammonia LT. Such PRM (herein after designated as "Elevating PRM") has a positive effect on the reduction of the ammonia malodor.

In a preferred aspect of the invention, a PRM is identified as an Elevating PRM when such PRM is identified as elevating the ammonia LT by at least 20%, as judged by at least 60% of the panellists participating in the evaluation of step a). More preferably, the PRM is identified as elevating the ammonia LT by at least 20%, as judged by all the panellists participating in such evaluation.

In another preferred aspect of the invention, the PRMs are identified Elevating PRMs provided that they at least doubled the LT of ammonia for at least 60%, most preferably for all the panellists participating in the panel evaluation of step a).

Examples of PRMs meeting any of these criteria can be found in the examples below. In particular, examples of PRMs identified as being Elevating PRMs include isopropylmethyl butyrate, safranal, citronellol, linalool, butyl acetate, alpha-bisabolol, carvone, Exaltolide® (pentadecanolide, origin: Firmenich SA, Geneva, Switzerland), Fructalate® (diethyl1,4-cyclohexane dicarboxylate, origin: Firmenich SA, Geneva, Switzerland), Koumalactone® ((3aRS,6SR,7aSR)-perhydro-3,6-dimethyl-benzo[B]furan-2-one, origin: Firmenich SA, Geneva, Switzerland), methyl benzoate, dihydroestragole, allyl heptanoate and hydroxycitronellal, among which isopropylmethyl butyrate, safranal, citronellol, butyl acetate, alpha-bisabolol, carvone, Exaltolide® (pentadecanolide, origin: Firmenich SA, Geneva, Switzerland), Fructalate® (diethyl1,4-cyclohexane dicarboxylate, origin: Firmenich SA, Geneva, Switzerland), Koumalactone® ((3aRS, 6SR,7aSR)-perhydro-3,6-dimethyl-benzo[B]furan-2-one, origin: Firmenich SA, Geneva, Switzerland), methyl benzoate and allyl heptanoate are mostly preferred.

In step c), the PRMs identified as Elevating PRMs as described in any aspect of step b) above are combined to create a perfume. The Elevating PRMs are combined with each other and optionally with other PRMs, which did not prove to be increasing PRMs, provided that at least 50% by weight, relative to the total weight of the perfume, consists of increasing PRMs. In a preferred aspect of the invention, the perfume comprises at least 60% by weight, preferably at least 70% by weight, more preferably at least 80% by weight and most preferably at least 90% by weight, relative to the total weight of the perfume, of Elevating PRMs. Most preferably it entirely consists of Elevating PRMs.

In an even more preferred aspect of the invention, it is desirable to limit the amount of ingredients capable of lowering the LT of ammonia in the perfume, or even to completely avoid such PRMs. Therefore, in a preferred aspect of the invention, the method further comprises the step of identifying the PRMs which lower the ammonia LT by at least 20%, as judged by at least 60% of the panellists participating in the evaluation of step a) (hereinafter designated as Lowering PRMs). In any aspect of the invention, it is preferable that the perfume created in step c) comprises at most 20% by weight, preferably at most 10% by weight, more preferably at most 5% by weight, relative to the total weight of the perfume, of Lowering PRMs. Most preferably it is free of Lowering PRMs.

Most preferred perfumes created in step c) comprise at least 40%, preferably at least 50%, more preferably at least 60%, even more preferably 70% of Elevating PRMs. Most preferably the perfume consists of Elevating PRMs. In another preferred embodiment, the perfume comprises at most 10%, preferably at most 5% of Lowering PRMs. More preferably, they comprise at least 70% of Elevating PRMs and at most 5% of Lowering PRMs. Such perfumes are another object of the present invention. The Elevating and Lowering PRMs are as defined in the method of the invention.

When the perfume does not consists of Elevating PRMs only, the remainder of the composition can contain PRMs for which the influence on the ammonia LT has not been assessed or PRMs which have been assessed according to any specific aspect of step a) as being neither elevating PRMs, nor lowering PRMs. In a preferred aspect of the invention, the remainder of the composition is selected from the latter, so as to use only PRMs which have been assessed for their influence on the LT of ammonia.

In step d), the perfume thus created can be incorporated in any type of consumer product comprising ammonia. This is for example particularly useful in hair care products such as liquid and cream hair colorants, hair mousse, hair tonic including hair and scalp conditioners and other hair preparations including heat setting wave solutions and in home care products such as glass and window cleaners, hard surface cleaners, liquid floor polish, laundry pre-spotter and stain removers. The perfume can also be used in water-based interior and exterior paints and tinting bases as well as in water-based interior and exterior under-coaters and primers. It can also be used in products where ammonia is generated in situ, particularly where ammonia is released by the decomposition of urea in urine. Such products include pet litters such as non-clumping conventional litters, clumping litters, biodegradable litters and silica-gel litters, diapers and adult incontinence products.

The perfume can also be applied to any surface on which ammonia is deposited or is likely to be deposited, such as hair, windows or tiles treated with an ammonia-containing product. The perfume can be applied to the surface together with other components such as cleaning agents.

The perfume can also be applied to the air surrounding a surface to which ammonia is applied or is likely to be applied. In such case, the perfume is applied using any device suitable for diffusing the perfume into the air, such as a spray or an air freshener of any type.

The amount of perfume created in step c) that is applied to a consumer product varies depending on the product type. It is typically applied to a consumer product base in an amount of between 0.02 and 5% by weight. In hair care product, such as for example hair colorants, it is preferably applied in an amount of between 0.1 to 1.5% by weight, more preferably between 0.3 and 0.75% by weight. In glass and window cleaners, the perfume is preferably applied in an amount of between 0.05 and 0.15% by weight and in other hard surface cleaners, it is preferably applied in an amount of between 0.2 and 0.7% by weight. In solid products where ammonia is generated in situ, such as for example pet litter, the perfume is preferably applied in an amount of between 0.02 and 0.5% by weight, more preferably between 0.05 and 0.1% by weight. These percentages are all defined relative to the total weight of the consumer product base.

In the case where the perfume is applied to a solid consumer product base where ammonia is generated in situ by urine deposit, the perfume can advantageously be encapsulated in water or moisture soluble capsules which release the perfume in the presence of water or moisture. Preferably, it is encapsulated in modified starch-based capsules. Such capsules are well known to the person skilled in the art. Examples of such capsules are described in WO 03/043728. The perfume is preferably comprised in such capsules in an amount of between 30 and 50% by weight, based on the total weight of the capsules.

DESCRIPTION OF THE DRAWINGS

FIG. 1 represents the results of a sensory evaluation of the counteraction of ammonia malodor by the method of the invention, as carried out in Example 1. The counteraction of ammonia malodor using the method of the invention (Tank 2) is compared to the counteraction by perfumes used in conventional methods (Tanks 1 and 3). The ammonia malodor was also evaluated (Tank 4). The intensity of each perfume used in the comparison is also represented (Tanks 5, 6 and 7).

EXAMPLE

Method According to the Invention
a) Panel Evaluation of the LT of Ammonia Alone and of Ammonia in Combination with PRMs
Preparation of the Ammonia Stimulus An ammonia stimulus test range was prepared. To ensure a stable level of ammonia in each stimulus, the ammonia headspace was stabilized by combining appropriate concentrations of $NH_4Cl$, NaOH and $H_2O$ instead of simply adding ammonia directly to a solvent. Different concentrations of ammonia were used to create a stimulus test range by utilizing the appropriate amount of each compound (see Table 1).

TABLE 1

Ammonia stimulus concentrations

| Simulus level | $NH_4Cl$ (ppm) | NaOH (ppm) | $NH_3$ vapor (ppm) * |
|---|---|---|---|
| 1 | 3390.00 | 2560.00 | 342.00 |
| 2 | 1360.00 | 1030.00 | 109.00 |
| 3 | 678.00 | 1030.00 | 34.70 |
| 4 | 339.00 | 513.00 | 11.10 |
| 5 | 136.00 | 205.00 | 3.53 |
| 6 | 67.80 | 103.00 | 1.12 |
| 7 | 33.90 | 51.30 | 0.36 |
| 8 | 13.60 | 20.50 | 0.11 |
| 9 | 6.78 | 10.25 | 0.04 |

* As calculated by Smeets, M. A. M., Bulsing P. J., Van Rooden, S., Steinmann, R., De Ru J. A., Ogink N. W. M., Van Thriel, C., Dalton, P. H.; O Chem. Senses 32 (2007) pp. 11-20

Preparation of the PRMs Stimuli

A stimulus was also prepared for each PRM which was intended to be combined with ammonia stimuli. As the PRMs differed in their potency and to ensure that each PRM stimulus had approximately the same potency, an abbreviated dose response curve was constructed for each PRM by having four panellists evaluate the intensity of five concentration levels of the PRM dissolved in propylene glycol in duplicate. Assessments were made relative to the reference of 170 ppm allyl heptanoate in propylene glycol, which intensity was set to 0. Based upon the average scores, a rough intensity match was made for each PRM utilizing one of the following criteria. If one of the tested concentration levels averaged at or near zero, this concentration level was selected. If the rating created any sort of reasonable curve, the equation of the curve was determined and solved for 0 to arrive at the PRM assessment level. If multiple concentration levels were equally distant form the match level, then the standard deviation across individuals was considered, as were the individual responses. In general, the PRM level was selected to be on average close to 0 with low variability, with two panellists saying the level was a bit too high and the other two panellists saying the level was a bit too low. The PRMs for which a stimulus was prepared are listed in Table 2 below, together with the concentration of the PRM in the stimulus.

TABLE 2

Composition of the PRM stimuli

| PRM | Concentration (ppm) |
|---|---|
| Isopropylmethyl butyrate | 90 |
| Safranal | 140 |
| Citronellol | 2500 |

TABLE 2-continued

Composition of the PRM stimuli

| PRM | Concentration (ppm) |
|---|---|
| Butyl acetate | 470 |
| Alpha-bisabolol | 25000 |
| Carvone | 3600 |
| Exaltolide ®[1] | 100 |
| Fructalate ®[2] | 2800 |
| Koumalactone ®[3] | 1000 |
| Methyl Benzoate | 200 |
| Allyl heptanoate | 170 |
| Linalool | 230 |
| Hydroxycitronellal | 340 |
| Dihydroestragole | 30 |
| Paradisone ®[4] | 156 |
| Lilial ®[5] | 500 |
| Florol ®[6] | 32750 |
| Aladinate ®[7] | 520 |
| (Z)-3-hexen-1-ol | 300 |
| Heliotropine[8] | 1000 |
| Lilyflore ®[9] | 1000 |
| Hedione ®[10] | 2500 |
| Cetalox ®[11] | 700 |
| Delta damascone[14] | 5000 |
| Agrudienes | 25 |
| Cedrenol | 2500 |
| Hexyl salicylate | 100 |
| Iralia ®[12] | 100 |
| Applinate[13] | 60 |
| Aphermate | 1000 |
| Geraniol | 1500 |
| Creosol H | 10 |

[1] Pentadecanolide, origin: Firmenich SA, Geneva, Switzerland
[2] Diethyl 1,4-cyclohexane dicarboxylate, origin: Firmenich SA, Geneva, Switzerland
[3] (3aRS,6SR,7aSR)-perhydro-3,6-dimethyl-benzo[B]furan-2-one, origin: Firmenich SA, Geneva, Switzerland
[4] (+)-Methyl (1R)-cis-3-oxo-2-pentyl-1-cyclopentaneacetate, origin: Firmenich SA, Geneva, Switzerland
[5] 3-(4-Tert-butylphenyl)-2-methylpropanal, origin: Givaudan SA, Vernier, Switzerland
[6] Tetrahydro-2-isobutyl-4-methyl-4(2H)-pyranol, origin: Firmenich SA, Geneva, Switzerland
[7] (Z)-3-methyl-2-hexenyl acetate, origin: Firmenich SA, Geneva, Switzerland
[8] 1,3-Benzodioxole-5-carbaldehyde, origin: Firmenich SA, Geneva, Switzerland
[9] 2,5-Dimethyl-2-indanmethanol, origin: Firmenich SA, Geneva, Switzerland
[10] Methyl dihydrojasmonate, origin: Firmenich SA, Geneva, Switzerland
[11] Dodecahydro-3a,6,6,9a-tetramethyl-naphtho[2,1-b]furan, origin: Firmenich SA, Geneva, Switzerland
[12] Mixture of methylionone isomers, origin: Firmenich SA, Geneva, Switzerland
[13] Ethyl 2-methyl-pentanoate, origin: Firmenich SA, Geneva, Switzerland
[14] Origin: Firmenich SA, Geneva, Switzerland.

Selection of the Panellists

Volunteers were screened for their ability to lateralize ammonia stimuli. For the screening, the experimenter measured the participant's lateralization threshold for ammonia using a two-alternative forced choice modified staircase procedure employing a four-in, two-down, one-up rule with a five reversal criterion, as described below, On each trial volunteers were presented with a pair of glass bottles with clean, custom-made nose pieces. One bottle contained ammonia at a particular level selected from Table 1 and the other bottle contained water only. Each bottle was applied to one nostril using the nose piece. The volunteers were asked to identify which bottle in each pair contained ammonia.

If the ammonia stimulus was correctly identified in four consecutive trials, the concentration was decreased by one level of Table 1 on the next trial. If an incorrect answer was provided, the concentration was increased by one level of Table 1. Location (left or right nostril) of the stimulus was randomized over presentations. Testing continued until one of the following occurred:
1) Five reversals (correct decision followed by an incorrect decision or vice versa) were achieved;
2) The volunteer gave a correct response twice in a row at the lowest level of Table 1; or 3) The volunteer gave an incorrect response at the highest level of Table 1.

In the first circumstance, threshold values were then calculated by averaging the last four reversals. In the second circumstance, the LT was the lowest level. In the third circumstance, the LT could not be calculated. Volunteers were considered qualified to participate in the panel evaluation if their LT could be calculated (Circumstance 1).

Panel Evaluation of the LT of Ammonia Alone and in Combination with a PRM.

The LT of ammonia, both alone and in combination with diverse PRM, was determined. A repeated-measures design was used, such that the LT with and without the addition of a PRM were both measured at the same time in one person by utilizing interwoven stimuli presentations. The LT for each PRM was measured by two to three panellists, the third panellists being included if the results of the first to panellists disagreed.

In a first round of evaluation two qualified panellists were involved in a panel evaluation of the LT of ammonia in two different conditions. For both conditions, the panellists were presented with a pair of samples. Each sample was in the form of a yoked two-bottle system, whereby two bottles were joined via tubing to a single nosepiece.

In the first condition (cond I), in the first sample, one bottle of the system contained an ammonia stimulus of one level selected from Table 1 and the other bottle contained propylene glycol alone. In the second sample one bottle contained water alone and the other one propylene glycol alone.

In the second condition (cond II), in the first sample, one bottle of the system contained an ammonia stimulus of one level selected from Table 1 and the other bottle contained one of the PRM stimuli of Table 2. In the second sample, one bottle contained water alone and the other one propylene glycol alone. This condition was assessed for each PRM stimulus of Table 2.

The panellists were asked to identify which sample in each pair contained ammonia. The LTs for each condition were collected simultaneously, alternating between the two conditions in an "abba baab" pattern. A two-alternative forced choice modified staircase procedure employing a two-down, one-up rule was used for the evaluation, as described below In order to minimize the build-up of ammonia in the nasal epithelium, the maximum number of stimulus presentations was capped at 25. Thus, a three-in rule with three reversal criterion was used. If both LTs were not collected in 25 or less presentations, the session was repeated until this limitation was met, typically starting at a slightly higher level of ammonia than in the previous session.

The three criteria applied for determination of ammonia LT in the panellists selection phase were applied, except that in the first circumstance three reversals were sufficient.

The ammonia LT in both conditions was then compared. In cases where both panellists did not agree on the effect of a particular PRM on the LT of ammonia (i.e. when one panellist evaluated that the LT of ammonia was lower for ammonia alone than for ammonia in combination with a specific PRM, while the other panellist found the contrary) or when one panellist found the same LT in both conditions, the evaluation of the LT in both conditions was carried out again with a third qualified panellist, using exactly the same procedure.

The results of the evaluation carried out are summarized in Table 3 below.

TABLE 3

Results of panel evaluation of the LT of ammonia alone and in combination with a PRM

| | Ammonia LT (ppm) | | | | | | | | |
|---|---|---|---|---|---|---|---|---|---|
| | Panellist 1 | | | Panellist 2 | | | Panellist 3 | | |
| PRM | Cond I | Cond II | % Δ | Cond I | Cond II | % Δ | Cond I | Cond II | % Δ |
| Isopropylmethyl butyrate | 0.2 | 188.4 | 81809 | 56.3 | 188.3 | 235 | | | |
| Safranal | 19.1 | 22.9 | 20 | 6.9E−05 | 2.2E−03 | 3088 | | | |
| Citronellol | 2.0 | 60.0 | 2978 | 188.3 | 225.5 | 20 | | | |
| Butyl acetate | 2.3 | 7.3 | 213 | 19.1 | 225.5 | 1079 | | | |
| Alpha-bisabolol | 2.3 | 7.3 | 213 | 22.9 | 172.7 | 655 | | | |
| Carvone | 6.1 | 19.1 | 214 | 71.9 | 225.5 | 214 | | | |
| Exaltolide ®[1] | 2.0 | 6.1 | 213 | 22.9 | 71.9 | 214 | | | |
| Fructalate ®[2] | 19.1 | 56.3 | 194 | 60 | 188.3 | 214 | | | |
| Koumalactone ®[3] | 7.3 | 19.1 | 162 | 22.9 | 71.9 | 214 | | | |
| Methyl benzoate | 2.3 | 7.3 | 213 | 22.9 | 60 | 162 | | | |
| Allyl heptanoate | 56.3 | 71.9 | 28 | 188.3 | 225.5 | 20 | | | |
| Linalool | 7.3 | 188.3 | 2480 | 22.9 | 22.9 | 0 | 17.9 | 56.3 | 214 |
| Hydroxycitronellal | 60.0 | 71.9 | 20 | 71.9 | 56.1 | −22 | 19.1 | 22.9 | 20 |
| Dihydroestragole | 19.1 | 7.3 | −62 | 56.3 | 71.9 | 28 | 7.3 | 22.9 | 214 |
| Paradisone ®[4] | 22.9 | 22.9 | 0 | 71.7 | 225.5 | 214 | 22.9 | 6.1 | −73 |
| Lilial ®[5] | 5.7 | 22.9 | 300 | 188.3 | 7.3 | −96 | 19.1 | 19.1 | 0 |
| Florol ®[6] | 22.9 | 56.3 | 146 | 19.1 | 7.3 | −62 | 22.9 | 22.9 | 0 |
| Aladinate ®[7] | 22.9 | 19.1 | −16 | 71.9 | 71.9 | 0 | | | |
| (Z)-3-hexen-1-ol | 7.3 | 2.3 | −68 | 225.5 | 225.5 | 0 | 7.3 | 56.3 | 671 |
| Heliotropine ®[8] | 2.0 | 7.3 | 274 | 172.7 | 22.9 | −87 | 60.0 | 2.3 | −96 |
| Lilyflore ®[9] | 22.9 | 60.0 | 162 | 188.3 | 176.5 | −6 | 45.8 | 7.3 | −84 |
| Hedione ®[10] | 6.1 | 7.5 | 23 | 225.5 | 22.9 | −90 | 19.1 | 6.1 | −68 |
| Cetalox ®[11] | 22.9 | 2.3 | −90 | 7.3 | 225.5 | 2988 | 7.3 | 2.3 | −68 |
| Delta damascone ®[14] | 22.9 | 7.3 | −68 | 71.9 | 225.5 | 214 | 176.5 | 7.3 | −96 |
| Agrudienes | 19.1 | 1.8 | −90 | 60.0 | 188.3 | 214 | 22.9 | 19.1 | −16 |
| Cedrenol | 7.3 | 2.3 | −68 | 22.9 | 60 | 162 | 56.3 | 2.3 | −96 |
| Hexyl salicylate | 22.9 | 7.3 | −68 | 71.9 | 188.3 | 162 | 19.1 | 7.3 | −62 |
| Iralia ®[12] | 17.9 | 7.3 | −59 | 71.9 | 60.0 | −16 | | | |
| Applinate ®[13] | 6.1 | 2.3 | −62 | 71.9 | 55.1 | −23 | | | |

TABLE 3-continued

Results of panel evaluation of the LT of ammonia alone and in combination with a PRM

| | Ammonia LT (ppm) | | | | | | | | |
|---|---|---|---|---|---|---|---|---|---|
| | Panellist 1 | | | Panellist 2 | | | Panellist 3 | | |
| PRM | Cond I | Cond II | % Δ | Cond I | Cond II | % Δ | Cond I | Cond II | % Δ |
| Aphermate | 19.1 | 6.1 | −68 | 176.5 | 71.9 | −59 | | | |
| Geraniol | 19.1 | 6.1 | −68 | 225.5 | 60.0 | −73 | | | |
| Creosol H | 56.3 | 17.9 | −68 | 71.9 | 7.3 | −90 | | | |

[1] Pentadecanolide, origin: Firmenich SA, Geneva, Switzerland
[2] Diethyl 1,4-cyclohexane dicarboxylate, origin: Firmenich SA, Geneva, Switzerland
[3] (3aRS,6SR,7aSR)-perhydro-3,6-dimethyl-benzo[B]furan-2-one, origin: Firmenich SA, Geneva, Switzerland
[4] (+)-Methyl (1R)-cis-3-oxo-2-pentyl-1-cyclopentaneacetate, origin: Firmenich SA, Geneva, Switzerland
[5] 3-(4-Tert-butylphenyl)-2-methylpropanal, origin: Givaudan SA, Vernier, Switzerland
[6] Tetrahydro-2-isobutyl-4-methyl-4(2H)-pyranol, origin: Firmenich SA, Geneva, Switzerland
[7] (Z)-3-methyl-2-hexenyl acetate, origin: Firmenich SA, Geneva, Switzerland
[8] 1,3-Benzodioxole-5-carbaldehyde, origin: Firmenich SA, Geneva, Switzerland
[9] 2,5-Dimethyl-2-indanmethanol, origin: Firmenich SA, Geneva, Switzerland
[10] Methyl dihydrojasmonate, origin: Firmenich SA, Geneva, Switzerland
[11] Dodecahydro-3a,6,6,9a-tetramethyl-naphtho[2,1-b]furan, origin: Firmenich SA, Geneva, Switzerland
[12] Mixture of methylionone isomers, origin: Firmenich SA, Geneva, Switzerland
[13] Ethyl 2-methyl-pentanoate, origin: Firmenich SA, Geneva, Switzerland
[14] Origin: Firmenich SA, Geneva, Switzerland.

Using the same method as described above, the results of Table 4 were also obtained.

TABLE 4

Results of panel evaluation of the LT of ammonia alone and in combination with a PRM

| | Panellist 1 | | | Panellist 2 | | | Panellist 3 | | |
|---|---|---|---|---|---|---|---|---|---|
| PRM | Cond I | Cond II | %Δ | Cond I | Cond II | %Δ | Cond I | Cond II | %Δ |
| (+)-(3S,3AS,6R,7AR)-perhydro-3,6-dimethyl-benzo[B]furan-2-one[1] | 2.0 | 19.6 | 885 | 0.1 | 3.5 | 4929 | 0.6 | 11.1 | 1682 |
| Romascone ®[2] | 0.6 | 11.1 | 1685 | 1.1 | 2.0 | 77 | 0.4 | 6.3 | 1686 |
| Ethyl (2E)-2,4,7-decatrienoate[3] | 0.4 | 1.1 | 223 | 0.4 | 2.0 | 469 | 0.1 | 2.0 | 2743 |
| Beta Dorinone ®[4] | 3.5 | 11.1 | 214 | 2.0 | 19.6 | 885 | 0.1 | 2.0 | 1558 |
| 2-cyclohexylethyl acetate | 0.2 | 2.0 | 848 | 0.2 | 1.1 | 465 | 0.1 | 1.1 | 842 |
| Helvetolide ®[5] | 2.0 | 11.1 | 454 | 0.4 | 2.0 | 426 | 0.2 | 2.0 | 895 |
| Gamma damascone[6] | 2.0 | 6.3 | 214 | 2.0 | 19.6 | 885 | 2.0 | 11.1 | 456 |
| 5-ethyl-2-nonanol | 2.0 | 19.6 | 885 | 1.1 | 6.2 | 452 | 2.0 | 6.3 | 214 |
| Ethyl 3-methyl-2-oxopentanoate[7] | 0.1 | 0.6 | 417 | 0.1 | 0.6 | 786 | 0.2 | 0.6 | 210 |
| 2-Methyl-4-(2,2,3-trimethyl-3-cyclopenten-1-yl)-4-penten-1-ol[8] | 1.1 | 3.5 | 212 | 1.1 | 3.5 | 212 | 0.2 | 2.0 | 852 |
| Mayol ®[9] | 0.1 | 0.6 | 800 | 1.1 | 3.5 | 212 | 1.1 | 3.5 | 212 |
| Ethyl 2,6,6-trimethyl-1,3-cyclohexadiene-1-carboxylate[10] | 0.1 | 0.6 | 786 | 0.2 | 0.6 | 215 | 0.1 | 0.2 | 200 |
| Floralozone[11] | 0.2 | 2.0 | 895 | 2.0 | 6.3 | 214 | 2.0 | 3.5 | 77 |
| 7-Propyl-2H,4H-1,5-benzodioxepin-3-one[12] | 2.0 | 11.1 | 456 | 1.1 | 6.3 | 453 | 1.1 | 3.5 | 212 |
| 2-Ethyl-4,4-dimethyl-1-cyclohexanone[13] | 1.1 | 3.5 | 212 | 0.4 | 2.0 | 471 | 0.6 | 2.0 | 217 |
| Cyclogalbanate[14] | 0.6 | 2.0 | 216 | 1.1 | 6.3 | 453 | 1.1 | 3.5 | 212 |
| Muscenone ™[15] | 2.0 | 11.1 | 454 | 6.2 | 11.1 | 77 | 3.5 | 11.1 | 214 |
| (+)-(1S,2S,3S)-2,6,6-Trimethyl-bicyclo[3.1.1]heptane-3-spiro-2'-cyclohexen-4'-one[16] | 0.2 | 0.4 | 75 | 0.1 | 0.6 | 417 | 0.2 | 0.6 | 215 |
| Sclareolate ®[17] | 0.2 | 1.1 | 465 | 0.4 | 1.1 | 223 | 0.6 | 0.6 | −2 |
| Cis-2-pentyl-1-cyclopentanol[18] | 0.6 | 2.0 | 216 | 0.2 | 0.4 | 90 | 1.1 | 3.5 | 212 |

TABLE 4-continued

Results of panel evaluation of the LT of ammonia alone and in combination with a PRM

| PRM | Panellist 1 | | | Panellist 2 | | | Panellist 3 | | |
|---|---|---|---|---|---|---|---|---|---|
| | Cond I | Cond II | %Δ | Cond I | Cond II | %Δ | Cond I | Cond II | %Δ |
| Ethyl 2-methylbutanoate | 6.2 | 19.6 | 214 | 3.5 | 11.1 | 213 | 6.2 | 11.1 | 77 |
| 3,7-Dimethyl-1-octanol | 2.0 | 6.3 | 214 | 2.0 | 3.5 | 77 | 2.0 | 3.5 | 77 |
| Myrrhone ®[19] | 6.3 | 11.1 | 77 | 1.1 | 3.5 | 212 | 2.0 | 3.5 | 77 |

[1] Origin: Firmenich SA, Geneva, Switzerland;
[2] Methyl 2,2-dimethyl-6-methylene-1-cyclohexanecarboxylate, origin: Firmenich SA, Geneva, Switzerland;
[3] Origin: Firmenich SA, Geneva, Switzerland;
[4] 1-(2,6,6-trimethyl-1-cyclohexen-1-yl)-2-buten-1-one, origin: Firmenich SA, Geneva, Switzerland
[5] (+)-(1S,1'R)-2-[1-(3',3'-dimethyl-1'-cyclohexyl)ethoxy]-2-methylpropyl propanoate, origin: Firmenich SA, Geneva, Switzerland
[6] (+−)-(E)-1-(2,2-dimethyl-6-methylene-1-cyclohexyl)-2-buten-1-one, origin: Firmenich, Geneva, Switzerland
[7] Origin: Firmenich SA, Geneva, Switzerland;
[8] Origin: Firmenich SA, Geneva, Switzerland;
[9] cis-7-P-menthanol, origin: Firmenich SA, Geneva, Switzerland
[10] Origin: Firmenich SA, Geneva, Switzerland;
[11] Mixture of 3-(4-ethylphenyl)-2,2-dimethylpropanal and 3(2-ethylphenyl)-2,2-dimethylpropanal, origin: International Flavors and Fragrances, USA
[12] Origin: Firmenich SA, Geneva, Switzerland;
[13] Origin: Firmenich SA, Geneva, Switzerland;
[14] Allyl (cyclohexyloxy)-acetate, origin: Dragoco, Holzminden, Germany
[15] 3-Methyl-(4/5)-cyclopentadecenone, origin: Firmenich SA, Geneva, Switzerland
[16] Origin: Firmenich SA, Geneva, Switzerland;
[17] Propyl (S)-2-(1,1-dimethylpropoxy)propanoate, origin: Firmenich SA, Geneva, Switzerland
[18] Origin: Firmenich SA, Geneva, Switzerland
[19] Mixture of (E)-4-(2,2,C-3,T-6-tetramethyl-R-1-cyclohexyl)-3-buten-2-one and (E)-4-(2,2,T-3,T-6-tetramethyl-R-1-cyclohexyl)-3-buten-2-one b) Identification of PRMs Ability to Affect the LT of Ammonia The following materials were identified as being capable of elevating the LT of ammonia by at least 20% for at least two over two or three panellists (see Tables 3 and 4): isopropyl-methyl butyrate, safranal, citronellol, linalool, butyl acetate, alpha-bisabolol, carvone, Exaltolide® (pentadecanolide, origin: Firmenich SA, Geneva, Switzerland), Fructalate® (diethyl 1,4-cyclohexane dicarboxylate, origin: Firmenich SA, Geneva, Switzerland), Koumalactone® ((3aRS,6SR,7aSR)-perhydro-3,6-dimethyl-benzo[B]furan-2-one, origin: Firmenich SA, Geneva, Switzerland), methyl benzoate, dihydroestragole, allyl heptanoate and hydroxycitronellal.

c) Creation of a Perfume

A perfume (Elevating Perfume) was prepared having the following ingredients in the amount indicated:

TABLE 5

Composition of the Elevating perfume

| PRM | Amount [%] |
|---|---|
| Allyl heptanoate | 10.0 |
| Butyl acetate | 5.0 |
| Carvone | 5.0 |
| Citronellol | 20.0 |
| Exaltolide ®[1] | 20.0 |
| Fructalate ®[2] | 5.0 |
| Hydroxycitronellal | 10.0 |
| Linalool | 20.0 |
| Methyl benzoate | 5.0 |

[1] Pentadecanolide, origin: Firmenich SA, Geneva, Switzerland
[2] Diethyl 1,4-cyclohexane dicarboxylate, origin: Firmenich SA, Geneva, Switzerland d) Application of the Perfume to the Headspace of a Hair Colouring Product Base Comprising Ammonia In order to assess the effect of the perfume prepared above on the reduction of ammonia malodor perception, the effect of this perfume was compared to the effect of two other perfumes. The first one was prepared with PRMs identified as being Lowering PRMs (i.e. identified as lowering the LT of ammonia by at least 20% according to two panellists over two or three as indicated in Tables 3 and 4 above) (Lowering Perfume). The Lowering Perfume contained the following ingredients, in the amounts indicated.

TABLE 6

Composition of Lowering Perfume

| PRM | Amount [%] |
|---|---|
| Applinate[1] | 4.0 |
| Cetalox ®[2] | 3.0 |
| Delta damascone[5] | 3.0 |
| Geraniol | 25.0 |
| Hexyl salicylate | 25.0 |
| Iralia ®[3] | 15.0 |
| Hedione ®[4] | 25.0 |

[1] Ethyl 2-methyl-pentanoate, origin: Firmenich SA, Geneva, Switzerland
[2] Dodecahydro-3a,6,6,9a-tetramethyl-naphtho[2,1-b]furan, origin: Firmenich SA, Geneva, Switzerland
[3] Mixture of methylionone isomers, origin: Firmenich SA, Geneva, Switzerland
[4] Methyl dihydrojasmonate, origin: Firmenich SA, Geneva, Switzerland
[5] Origin: Firmenich SA, Geneva, Switzerland The second of these other perfumes was a fragrance accord (Normal Fragrance) designed without taking the effect of its components on the ammonia LT. It was not specifically formulated with malodor counteracting PRMs, but simply created on the basis of hedonic (perfumistic) considerations. This fragrance contained only 2.8% by weight, based on the total weight of the fragrance of Elevating PRMs.

TABLE 7

Composition of the Normal Fragrance

| Ingredient | Amount [wt %] |
|---|---|
| Hexyl acetate | 0.57 |
| (Z)-3-hexenyl acetate | 0.07 |
| Prenyl acetate | 1.43 |
| Acetophenone | 0.03 |
| Decanal | 0.09 |
| Ambrettolide[1] | 0.43 |
| Anethol | 0.29 |
| Gamma undecalactone | 1.00 |
| Cetalox ®[2] | 0.21 |
| 4-Cyclohexyl-2-methyl-2-butanol | 8.57 |
| Mixture of tricyclo[5.2.1.0(2,6)]dec-3-en-8-yl acetate and tricyclo[5.2.1.0(2,6)]dec-4-en-8-yl acetate | 4.29 |
| Exaltolide ®[3] | 2.14 |
| Mixture of tetrahydro-4-methylene-2-phenylpyran and 3,6-dihydro-4-methyl-2-phenyl-2H-pyran | 0.14 |
| Cyclopentol[4] | 0.29 |
| Alpha Damascene[11] | 0.11 |
| (1'R,E)-2-ethyl-4-(2',2',3'-trimethyl-3'-cyclopenten-1'-yl)-2-buten-1-ol[5] | 1.43 |
| γ-n-Decalactone | 0.57 |
| Delta Damascene[11] | 0.06 |
| Dihydroterpineol | 2.86 |
| Dipropylene glycol | 19.38 |
| Ethyl linalool | 4.29 |
| Ethyl vanillin | 0.01 |
| Floralozone[6] | 0.21 |
| Heliotropine[7] | 0.43 |
| Allyl heptanoate | 0.57 |
| Phenoxy isobutyrate | 4.29 |
| (3Z)-3,4,5,6,6-pentamethyl-3-hepten-2-one | 2.86 |
| Cis-jasmone | 0.14 |
| Hedione ®[8] | 18.57 |
| Ethyl 2-methylbutanoate | 0.11 |
| Florol ®[9] | 2.14 |
| Phenetylol | 0.71 |
| 3-(6,6-Dimethyl-bicyclo[3.1.1]hept-2-en-2-yl)propanal | 0.03 |
| (Z)-3-hexen-1-ol | 0.04 |
| Hexyl salicylate | 8.57 |
| (Z)-3-Hexenyl 2-hydroxybenzoate | 1.43 |
| (+−)-3,7-Dimethyl-3-octanol | 4.29 |
| Verdox ®[10] | 7.14 |
| 2,4-Dimethyl-3-cyclohexene-1-carbaldehyde[11] | 0.21 |
| Total | 100.00 |

[1] Oxacycloheptadec-10-en-2-one
[2] Pentadecanolide, origin: Firmenich SA, Geneva, Switzerland
[3] Dodecahydro-3a,6,6,9a-tetramethyl-naphtho[2,1-b]furan, origin: Firmenich SA, Geneva, Switzerland
[4] Cis-2-pentyl-1-cyclopentanol, origin: Firmenich SA, Geneva. Switzerland
[5] Origin: Firmenich SA, Geneva, Switzerland
[6] Mixture of 3-(4-ethylphenyl)-2,2-dimethylpropanal and 3(2-ethylphenyl)-2,2-dimethylpropanal, origin: International Flavors and Fragrances, USA
[7] 1,3-Benzodioxole-5-carbaldehyde, origin: Firmenich SA, Geneva, Switzerland
[8] Methyl dihydrojasmonate, origin: Firmenich SA, Geneva, Switzerland
[9] Tetrahydro-2-isobutyl-4-methyl-4(2H)-pyranol
[10] 2-Tert-butyl-1-cyclohexyl acetate, origin: International Flavors & Fragrances, USA
[11] Origin: Firmenich SA, Geneva, Switzerland Four samples were prepared in 5.5 gal fish tanks having a 3" circular opening (Tanks 1 to 4). Each tank contained 0.6 g of a standard hair colour base comprising 6% of ammonia presented in two 0.3 g aliquots in open GC vial inserts.

Tank 1 further contained two open 2-oz flint jars, each containing 10 g of a 1% solution of the Normal Fragrance in propylene glycol.

Tank 2 further contained one open 2-oz flint jar containing 10 g of a 1% solution of the Elevating Perfume described in Table 5 above in propylene glycol and one open 2-oz flint jar containing 10 g of a 1% solution of the Normal Fragrance in propylene glycol.

Tank 3 further contained one open 2-oz flint jar containing 10 g of a 1% solution of the Lowering Perfume described in Table 6 above in propylene glycol and one open 2-oz flint jar containing 10 g of a 1% solution of the Normal Fragrance in propylene glycol.

Tank 4 further contained two open 2-oz flint jars containing 10 g of propylene glycol.

The relative efficacy of the Elevating and Lowering Perfumes at controlling ammonia malodor in the headspace of the hair colour base was assessed by 30 panellists on a blind basis. The panellists were asked to sniff the odor emanating from the opening of Tanks 1 to 4. They were asked to individually rank the odor emanating from the four tanks from weakest to strongest in ammonia odor intensity. Panellists were allowed to proceed at their own pace and to re-sniff as often as they liked until their rank order was set. After taking a short break, the panellists then re-smelled the tanks in the order of their ranking from weakest to strongest to confirm the order, making any necessary adjustments and repeating this step until the panellist was satisfied.

In addition, in a separate session, 28 panellists were asked to rank the relative intensities of the Elevating Perfume (Table 5 above), Lowering Perfume (Table 6 above) and Normal Fragrance.

Three samples were prepared in 5.5 gal fish tanks having a 3" circular opening (Tanks 5 to 7).

Tank 5 contained two open 2-oz flint jars, each containing 10 g of a 1% solution of the Normal Fragrance in propylene glycol.

Tank 6 contained one open 2-oz flint jar containing 10 g of a 1% solution of the Elevating Perfume and one open 2-oz flint jar containing 10 g of a 1% solution of the Normal Fragrance in propylene glycol.

Tank 7 further contained one open 2-oz flint jar containing 10 g of a 1% solution of the Lowering Perfume in propylene glycol and one open 2-oz flint jar containing 10 g of a 1% solution of the Normal Fragrance in propylene glycol.

The relative intensity of the Elevating Perfume, Lowering Perfume and Normal Fragrance was assessed by the panellists on a blind basis. They were asked to sniff the odor emanating from the opening of Tanks 5 to 7 and to individually rank the intensity of the perfumes emanating from the three tanks from weakest to strongest. Panellists were allowed to proceed at their own pace and to re-sniff as often as they liked until their rank order was set. After taking a short break, the panellists then re-smelled the tanks in the order of their ranking from weakest to strongest to confirm the order, making any necessary adjustments and repeating this step until the panellist was satisfied.

The results of each session were analysed using the Friedman's ANOVA for ordinal data. Before conducting the ANOVA of the ammonia malodor evaluation, five panellists who rated the ammonia control (Tank 4) as the weakest stimulus were excluded from further analysis.

The results of both analyses are represented in FIG. 1. These results show that the perceived intensity of the ammonia odor depends on both the intensity of the applied perfume and the presence of ingredients capable of elevating the LT of ammonia. The advantage of the method of the invention is demonstrated by the fact that even if the Elevating Perfume has the weakest fragrance intensity, this perfume proved to be the most efficient to counteract the ammonia malodor. To the contrary, the Normal Fragrance, which was not specifically designed with Elevating PRMs and in fact contained only very low amounts of Elevating PRMs, was unable to compensate its weaker intensity when compared to the Lowering Perfume.

The PRMs selected to be assessed for their ability to elevate the LT of ammonia according to step a) of the present examples were selected among PRMs already known to effectively cover the ammonia malodor from an olfactory/sensory point of view. This explains why the Lowering Perfume has been judged by the panel to already have an effect in counteracting malodor as shown in FIG. 1, and to improve upon the Normal Fragrance. In fact, the Normal Fragrance was not specifically formulated with malodor counteracting PRMs, but simply created on the basis of hedonic (perfumistic) considerations. As shown in FIG. 1, the Elevating Perfume prepared according to step c) of the present invention's method, proved even more efficient than the Lowering Perfume, thus providing evidence of the advantage of this method over the known methods to counteract ammonia malodor, which relied strictly on the capability of chemicals to cover the ammonia malodor or on the chemical conversion of malodorants into non-odorant or less odorant substances. Therefore, the method of the present invention enables a more accurate and specific selection of PRMs so as to optimize their activity to counteract ammonia malodor by assessing their trigeminal effect and fine tuning of perfumes for ammonia malodor counteraction based on such assessment.

The invention claimed is:

1. Method for counteracting ammonia malodor comprising:
   a) carrying out a panel evaluation of the lateralization threshold of ammonia in the presence and in the absence of a perfumery raw material (PRM) and comparing both lateralization thresholds;
   b) identifying PRMs which elevate the ammonia lateralization threshold when present with ammonia (Elevating PRMs), wherein the Elevating PRMs are identified as elevating the ammonia lateralization threshold by at least 20%, as judged by at least 60% of the panelists participating in the evaluation of step a);
   c) creating a perfume composition comprising at least 70% by weight, relative to the total weight of the perfume composition, of one or more of the Elevating PRMs identified in step b);
   d) applying the perfume composition created in step c) to a consumer product base comprising ammonia, to a surface on which ammonia is deposited or is likely to be deposited, to the air surrounding such surfaces or to surfaces or products susceptible of generating ammonia malodor in situ.

2. Method according to claim 1, further comprising the step of identifying the PRMs which lower the ammonia lateralization threshold by at least 20%, as judged by at least 60% of the panelists participating in the evaluation of step a) (Lowering PRMs).

3. Method according to claim 2, wherein the perfume composition created in step c) is free of Lowering PRMs.

4. Method according to claim 2, wherein the perfume composition created in step c) comprises at most 20% of Lowering PRMs.

5. Method according to claim 1, wherein the Elevating PRMs identified in step b) elevated the lateralization threshold of ammonia by at least 20% for all the panelists participating in the panel evaluation of step a).

6. Method according to claim 1, wherein the Elevating PRMs identified in step b) at least doubled the lateralization threshold of ammonia for at least 60% of the panelists participating in the panel evaluation of step a).

7. Method according to claim 6, wherein the Elevating PRMs identified in step b) at least doubled the lateralization threshold of ammonia for all panelists participating in the panel evaluation of step a).

8. Method according to claim 1, wherein the perfume composition created in step c) is used in combination with additional perfuming ingredients.

9. Method according to claim 1, wherein the perfume composition created in step c) is applied to a consumer product base comprising ammonia in an amount of between 0.02 and 5% by weight, relative to the total weight of the consumer product base.

10. Method according to claim 1 wherein the at least one Elevating PRM of the perfume composition is selected from the group consisting of isopropylmethyl butyrate, safranal, citronellol, linalool, butyl acetate, alpha-bisabolol, carvone, pentadecanolide, diethyl 1,4-cyclohexane dicarboxylate, (3 aRS,6SR,7aSR)-perhydro-3,6-dimethyl-benzo[B]furan-2-one, methyl benzoate, dihydroestragole, allyl heptanoate and hydroxycitronellal.

11. Method according to claim 1 wherein the at least one Elevating PRM of the perfume composition is diethyl 1,4-cyclohexane dicarboxylate.

* * * * *